United States Patent
Yoshida et al.

(10) Patent No.: US 6,388,089 B1
(45) Date of Patent: May 14, 2002

(54) BRASSINOSTEROID BIOSYNTHESIS INHIBITORS

(75) Inventors: Shigeo Yoshida, Tokyo; Shozo Fujioka, Saitama; Tadao Asami, Tokyo, all of (JP)

(73) Assignee: Riken, Saitama (JP)

( * ) Notice: Subject to any disclaimer, the term of this patent is extended or adjusted under 35 U.S.C. 154(b) by 0 days.

(21) Appl. No.: 09/744,958
(22) PCT Filed: Sep. 12, 1999
(86) PCT No.: PCT/JP99/04380
§ 371 Date: Apr. 18, 2001
§ 102(e) Date: Apr. 18, 2001
(87) PCT Pub. No.: WO00/09490
PCT Pub. Date: Feb. 24, 2000

(30) Foreign Application Priority Data

Aug. 12, 1998 (JP) ............................................ 10-227939

(51) Int. Cl.⁷ .................. C07D 249/08; A61K 31/4192
(52) U.S. Cl. ..................................... 548/262.2; 514/383
(58) Field of Search ........................ 548/262.2; 514/383

(56) References Cited

U.S. PATENT DOCUMENTS

| | | | |
|---|---|---|---|
| 4,104,399 A | * 8/1978 | Pommer et al. ............ 424/269 |
| 4,205,075 A | 5/1980 | Baldwin et al. |
| 4,243,405 A | 1/1981 | Balasubramanyan et al. |
| 4,578,396 A | 3/1986 | Jäger et al. |
| 4,940,481 A | 7/1990 | Müller et al. |
| 4,945,101 A | 7/1990 | Jäger et al. |
| 5,049,678 A | * 9/1991 | Baus et al. .............. 548/263.2 |
| 5,624,916 A | * 4/1997 | Shaber et al. ................ 514/63 |

FOREIGN PATENT DOCUMENTS

| | | |
|---|---|---|
| DE | 3222191 | 12/1983 |
| EP | 0025516 | 3/1981 |
| EP | 0091398 | 10/1983 |
| FR | 2365956 | 4/1978 |

OTHER PUBLICATIONS

Yong Ki Min, et al., "New Lead Compounds for Brassinosteroid Biosynthesis Inhibitors", *Bioorganic & Medicinal Chemistry Letters*, 9, pp. 425–430 (1999).
Yokota, *Trends In Plant Science*, vol. 2, No. 4, pp. 137–143 (1997).
Mandava, *Ann. Rev. Plant Physiol. Plant Mol. Biol.*, 39, pp. 23–52 (1988).
Schlagnhaufer et al., *Physiol. Plant.*, 61, pp. 555–558 (1984).
Iwasaki et al., *Plant Cell Physiol.*, 32 (7), pp. 1007–1014 (1991).
Yamamoto et al., *Plant Cell Physiol.*, 38 (8), pp. 980–983 (1997).
Azpiroz et al., *The Plant Cell*, vol. 10, pp. 219–230 (1998).
Clouse, *The Plant Journal*, 10 (1), pp. 1–8 (1996).
Fujioka et al., *Physiologia Plantarum*, 100, pp. 710–715 (1997).
Feldmann et al., *Science*, vol. 243, p. 1351–1354 (1989).
Takahashi et al., *Genes & Development*, 9, pp. 97–107 (1995).
Kauschmann et al., *The Plant Journal*, 9 (5), pp. 701–713 (1996).
Szekeres et al., *Cell*, vol. 85, pp. 171–182 (1996).
Li et al., *Science*, vol. 272, pp. 398–401 (1996).
Fujioka et al., *The Plant Cell*, vol. 9, pp. 1951–1962 (1997).
Nomura et al., *Plant Physiol*, 113, pp. 31–37 (1997).
Yokota et al., *Complicated Mechanism of Action of Uniconazoles*, pp. 339–349 (1991).
Wada et al., *Plant & Cell Physiol*, 22 (2), pp. 323–325 (1981).
Takatsuto, *Journal of Chromatography A*, 658, pp. 3–15 (1994).
Chory et al., *The Plant Cell*, vol. 3, pp. 445–459 (1991).

* cited by examiner

*Primary Examiner*—T. A. Solola
*Assistant Examiner*—Golam M. M. Shameem
(74) *Attorney, Agent, or Firm*—Greenblum & Bernstein, P.L.C.

(57) ABSTRACT

Compound represented by the following formula (I):

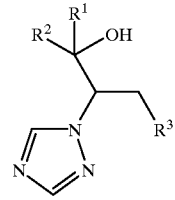

wherein $R^1$ represents a lower alkyl group, $R^2$ represents a phenyl group which may be substituted or a lower alkyl group and $R^3$ represents a phenyl group which may be substituted (e.g., 4-(4-chlorophenyl)-2-phenyl-3-(1,2,4-triazoyl)-butan-2-ol) or salts thereof. The compounds have a specific inhibitory action against the brassinosteroid biosynthesis, and are useful as plant growth regulators.

6 Claims, 2 Drawing Sheets

BRASSINOSTEROID BIOSYNTHESIS INHIBITORS

This application is a 371 of PCT/J99/04380, filed on Sep. 12, 1999.

TECHNICAL FIELD

The present invention relates to a compound having inhibitory action against the brassinosteroid biosynthesis and a plant growth regulator comprising said compound.

BACKGROUND ART

Brassinosteroids have recently recognized as a new class of plant hormones through the combination of molecular genetics and researches on biosyntheses (Yokota, Trends in Plant Sci., 2, pp.137–143, 1997). Since the chemistry of brassinosteroids was established, biological activities of these homologues have been extensively studied, and their notable actions on plant growth have been revealed, which include elongation of stalks, growth of pollen tubes, inclination of leaves, opening of leaves, suppression of roots, activation of proton pump (Mandava and Annu. Rev. Plant Physiol. Plant Mol. Biol., 39, pp.23–52, 1988), acceleration of ethylene production (Schlagnhaufer et al., Physiol. Plant, 61, pp.555–558, 1984), differentiation of vessel elements (Iwasaki et al., Plant Cell Physiol., 32, pp.1007–1014, 1991; Yamamoto et al., Plant Cell Physiol., 38, pp.980–983, 1997), and cell extension (Azpiroz et al., Plant Cell, 10, pp.219–230, 1998).

Furthermore, mechanisms and regulations of physiological actions of brassinosteroids have been being revealed by variety of studies on their biosynthesis (Clouse, Plant J. 10, pp.1–8, 1996; Fujioka et al., Physiol. Plant, 100, pp.710–715, 1997). At present, 40 or more brassinosteroids have been identified. Most of C28-brassinosteroids are common vegetable sterols, and they are considered to be biosynthesized from campesterol which has the same carbon side chain as that of brassinolide.

Some Arabidopsis mutants which show characteristic dwarfism have been isolated, i.e., dwf1: Feldman et al., Science, 243, pp.1351–1354, 1989; dim: Takahashi et al., Genes Dev., 9, pp.97–107, 1995; cbb1: Kauschmann et al., Plant J., 9, pp.701–703, 1996. Their structural photomorphogenesis and dwarfism (cpd; Szekeres et al., Cell, 85, pp.171–182, 1997) and de-etiolation (det2: Li et al., Science, 272, pp.398–401, 1996; Fujioka et al., Plant Cell, 9, pp.1951–1962, 1997) are known. The mutants have deficiencies in the brassinosteroid biosynthetic pathway. Further, a dwarf mutant of *Pisum sativum* was recently characterized, and the mutant was reported as a brassinosteroid deficient mutant (Nomura et al., Plant Physiol., 113, pp.31–37, 1997). In these plants, use of brassinolide is known to negate severe dwarfism of the mutants. Although these findings suggest that roles of brassinosteroids are indispensable for growth and development of plants, an effective tool other than the analysis of mutants has been desired to elucidate physiological importance of brassinolide.

As seen in researches of gibberellin action, specific inhibitors against the biosynthesis are generally very effective tools for elucidating physiological functions of endogenous substances. Specific inhibitors for the brassinosteroid biosynthesis are expected to provide a new tool for understanding the functions of brassinosteroids. Uniconazol is a potent plant growth regulator (PGR) which inhibits the oxidation employed by cytochrome P-450 in the steps of the gibberellin biosynthesis from ent-kaurene to ent-kaurenoic acid. Yokota et al. observed slight reduction of the amount of endogenous castasterone as a side effect of that compound (Yokota et al., "Gibberellin", Springer Verlag, N.Y., pp.339–349, 1991). Although uniconazole inhibits differentiation of vessel elements induced by brassinolide (Iwasaki et al., Plant Cell Physiol., 32, pp.1007–1014, 1991), its inhibitory action against brassinolide is considered to be no more than an incidental action, because uniconazol essentially inhibits the gibberellin biosynthesis.

DISCLOSURE OF THE INVENTION

An object of the present invention is to provide a specific inhibitor against the brassinosteroid biosynthesis. Some mutants which are deficient in enzymes for biosynthesis are known for Arabidopsis, and their morphologic changes are unique to mutants with deficiency in the brassinosteroid biosynthesis. Therefore, the inventors of the present invention conducted intensive search for a compound inducing the morphologic changes unique to the mutants with the brassinosteroid biosynthesis deficiency to find a specific inhibitor against the brassinosteroid biosynthesis. As a result, they found that the triazole compounds represented by the following formula (I) had the desired inhibitory action. The present invention was achieved on the basis of these findings.

The present invention thus provides a compound represented by the following formula (I):

wherein $R^1$ represents a lower alkyl group, $R^2$ represents a phenyl group which may be substituted or a lower alkyl group, and $R^3$ represents a phenyl group which may be substituted, or a salt thereof. According to a preferred embodiment of the present invention, there are provided the aforementioned compound or a salt thereof wherein $R^1$ is methyl group or ethyl group, and $R^2$ represents a phenyl group which may be substituted or tert-butyl group.

As another aspect of the present invention, there are provided an inhibitor against the brassinosteroid biosynthesis which comprises the compound represented by the aforementioned formula (I) or a physiologically acceptable salt thereof. The inhibitor of the present invention can be used as a plant growth regulator for, for example, suppression of plant elongation, suppression of pollen growth, retention of freshness of flowers, anti-stress agents for plants, weeds control, suppression of plant retrogradation, hypertrophism of roots and so forth.

According to further aspects of the present invention, there are provided a method for regulating plant growth by using the compound represented by the aforementioned formula (I) or a salt thereof; and use of the compound represented by the aforementioned formula (I) or a salt thereof for the manufacture of the aforementioned plant growth regulator.

BEST MODE FOR CARRYING OUT THE INVENTION

In the aforementioned formula (I), $R^1$ represents a lower alkyl group. As the lower alkyl group, a linear or branched alkyl group having 1 to about 6 carbon atoms can be used. Examples include methyl group, ethyl group, n-propyl group, isopropyl group, n-butyl group, sec-butyl group, tert-butyl group and so forth. The lower alkyl group represented by $R^1$ is preferably methyl group or ethyl group.

$R^2$ represents a phenyl group which may be substituted or a lower alkyl group. As the lower alkyl group represented by $R^2$, a linear or branched alkyl group having about 3 to about 6 carbon atoms is preferred, and a bulky alkyl group such as isopropyl group and tert-butyl group is preferred. When the phenyl group represented by $R^2$ or $R^3$ is substituted, types, numbers and substituting positions of substituents are not particularly limited. For example, the phenyl group may have preferably 1 to 3, more preferably 1 or 2 of substituents. Where the phenyl group has 2 or more substituents, they may be the same or different.

Examples of the substituent on the phenyl group include, for example, a halogen atom (any of fluorine atom, chlorine atom, bromine atom and iodine atom), a lower alkyl group (methyl group, ethyl group and the like), a lower cycloalkyl group (cyclopropyl group and the like), a halogenated lower alkyl group (trifluoromethyl group and the like), a lower alkoxy group (methoxy group, ethoxy group and the like), amino group, mono- or dialkylamino group, carboxyl group, an alkoxycarbonyl group (ethoxycarbonyl group and the like), an alkanoyl group (acetyl group and the like), an aroyl group (benzoyl group and the like), an aralkyl group (benzyl group and the like), an aryl group (phenyl group and the like), a heteroaryl group (pyridyl group and the like), heterocyclic group (pyrrolidinyl group and the like), hydroxyl group, nitro group, cyano group and so forth. However, the substituents are not limited to these examples. Among them, a halogen atom, a lower alkyl group, a halogenated lower alkyl group, a lower alkoxy group and so forth are preferred.

The compounds of the present invention have two asymmetric carbon atoms in the fundamental structure, and may have one or more further asymmetric carbon atoms depending on the type of the substituent. Optically active compounds and diastereoisomers in pure forms based on the asymmetric carbon atoms as well any mixtures of the isomers (for example, mixtures of two or more of diastereoisomers), racemates and so forth fall within the scope of the present invention. Further, the compounds of the present invention may form acid addition salts, and may further form acid addition salts depending on the type of the substituent. The types of the salts are not particularly limited, and examples of the salts include salts with mineral acids such as hydrochloric acid, and sulfuric acid, salts with organic acids such as p-toluenesulfonic acid, methanesulfonic acid, and tartaric acid, metal salts such as sodium salts, potassium salts, and calcium salts, ammonium salts, salts with organic amines such as triethylamine, salts with amino acids such as glycine and so forth.

Examples of the compounds of the present invention will be mentioned below. However, the compounds of the present invention are not limited to these examples. The symbols in the table represent: Me: methyl group; Et: ethyl group; MeO: methoxy group; tert-Bu: tertiary butyl group; and Ph: phenyl group. As for substituted phenyl groups, 4-Cl-Ph represents 4-chlorophenyl group; 2,4-di-Cl-Ph represents 2,4-dichlorophenyl group; 2-Cl-4-F-Ph represents 2-chloro-4-fluorophenyl group and so forth, and others are represented similarly.

TABLE 1

| Compound Number | $R^1$ | $R^2$ | $R^a$ |
|---|---|---|---|
| 1 (Diastereomer mixture) | Me | Ph | 4-Cl-Ph |
| 2 (Isomer I) | Me | Ph | 4-Cl-Ph |
| 3 (Isomer II) | Me | Ph | 4-Cl-Ph |
| 4 | Me | Ph | 4-Br-Ph |
| 5 | Me | Ph | 4-Br-Ph |
| 6 | Me | Ph | 2,4-di-Cl-Ph |
| 7 | Me | Ph | 3,4-di-Cl-Ph |
| 8 | Me | Ph | 4-Me-Ph |
| 9 | Me | Ph | 4-CF$_3$-Ph |
| 10 | Me | Ph | 3-Cl-Ph |
| 11 | Me | Ph | 3-MeO-Ph |
| 12 (Isomer I) | Me | 4-Cl-Ph | 4-Cl-Ph |
| 13 (Isomer II) | Me | 4-Cl-Ph | 4-Cl-Ph |
| 14 | Me | 4-Cl-Ph | 2,4-di-Cl-Ph |
| 15 (Isomer I) | Me | 4-F-Ph | 4-Cl-Ph |
| 16 (Isomer II) | Me | 4-F-Ph | 4-Cl-Ph |
| 17 | Me | 4-F-Ph | 2,4-di-Cl-Ph |
| 18 | Me | 4-F-Ph | 4-Me-Ph |
| 19 (Isomer I) | Me | 4-MeO-Ph | 4-Cl-Ph |
| 20 (Isomer II) | Me | 4-MeO-Ph | 4-Cl-Ph |
| 21 | Me | 4-MeO-Ph | 2,4-di-Cl-Ph |
| 22 | Et | Ph | 4-Cl-Ph |
| 23 (Isomer I) | Me | tert-Bu | 4-Cl-Ph |
| 24 (Isomer II) | Me | tert-Bu | 4-Cl-Ph |
| 25 | Me | tert-Bu | 2,4-di-Cl-Ph |
| 26 | Me | Ph | 4-F-Ph |
| 27 | Me | Ph | 2,4-di-F-Ph |
| 28 | Me | Ph | 2-Cl-4-F-Ph |
| 29 | Me | 4-Cl-Ph | 4-Br-Ph |
| 30 | Me | 4-Cl-Ph | 3,4-di-Cl-Ph |
| 31 | Me | 4-Cl-Ph | 4-Me-Ph |
| 32 | Me | 4-Cl-Ph | 4-CF$_3$-Ph |
| 33 | Me | 4-Cl-Ph | 3-Cl-Ph |
| 34 | Me | 4-Cl-Ph | 3-MeO-Ph |
| 35 | Me | 4-Cl-Ph | 4-F-Ph |
| 36 | Me | 4-Cl-Ph | 2,4-di-F-Ph |
| 37 | Me | 4-Cl-Ph | 2-Cl-4-F-Ph |
| 38 | Me | 4-F-Ph | 4-Br-Ph |
| 39 | Me | 4-F-Ph | 3,4-di-Cl-Ph |
| 40 | Me | 4-F-Ph | 4-CF$_3$-Ph |
| 41 | Me | 4-F-Ph | 3-Cl-Ph |
| 42 | Me | 4-F-Ph | 4-F-Ph |
| 43 | Me | 4-F-Ph | 3-MeO-Ph |
| 44 | Me | 4-F-Ph | 2,4-di-F-Ph |
| 45 | Me | 4-F-Ph | 2-Cl-4-F-Ph |
| 46 | Et | Ph | 2,4-di-Cl |
| 47 | Et | Ph | 4-Br-Ph |
| 48 | Et | Ph | 4-Me-Ph |
| 49 | Et | Ph | 3,4-di-Cl-Ph |
| 50 | Et | Ph | 4-CF$_3$-Ph |
| 51 | Et | Ph | 3-Cl-Ph |
| 52 | Et | Ph | 3-MeO-Ph |
| 53 | Et | Ph | 4-F-Ph |
| 54 | Et | Ph | 2,4-di-F-Ph |

TABLE 1-continued

| Compound Number | R¹ | R² | Rᵃ |
|---|---|---|---|
| 55 | Et | Ph | 2-Cl-4-F-Ph |
| 56 | Et | 4-Cl-Ph | 2,4-di-Cl-Ph |
| 57 | Et | 4-Cl-Ph | 4-Br-Ph |
| 58 | Et | 4-Cl-Ph | 3,4-di-Cl-Ph |
| 59 | Et | 4-Cl-Ph | 4-Me-Ph |
| 60 | Et | 4-Cl-Ph | 4-CF₃-Ph |
| 61 | Et | 4-Cl-Ph | 3-Cl-Ph |
| 62 | Et | 4-Cl-Ph | 3-MeO-Ph |
| 63 | Et | 4-Cl-Ph | 4-F-Ph |
| 64 | Et | 4-Cl-Ph | 2,4-di-F-Ph |
| 65 | Et | 4-Cl-Ph | 2-Cl-4-F-Ph |
| 66 | Et | 4-F-Ph | 4-Cl-Ph |
| 67 | Et | 4-F-Ph | 2,4-di-Cl-Ph |
| 68 | Et | 4-F-Ph | 4-Br-Ph |
| 69 | Et | 4-F-Ph | 3,4-di-Cl-Ph |
| 70 | Et | 4-F-Ph | 4-Me-Ph |
| 71 | Et | 4-F-Ph | 4-CF₃-Ph |
| 72 | Et | 4-F-Ph | 3-Cl-Ph |
| 73 | Et | 4-F-Ph | 3-MeO-Ph |
| 74 | Et | 4-F-Ph | 4-F-Ph |
| 75 | Et | 4-F-Ph | 2,4-di-F-Ph |
| 76 | Me | 2,4-di-Cl-Ph | 4-Cl-Ph |
| 77 | Me | 2,4-di-Cl-Ph | 2,4-di-Cl-Ph |
| 78 | Me | 2,4-di-Cl-Ph | 4-Br |
| 79 | Me | 2,4-di-Cl-Ph | 3,4-di-Cl-Ph |
| 80 | Me | 2,4-di-Cl-Ph | 4-Me-Ph |
| 81 | Me | 2,4-di-Cl-Ph | 4-CF₃-Ph |
| 82 | Me | 2,4-di-Cl-Ph | 3-Cl |
| 83 | Me | 2,4-di-Cl-Ph | 3-MeO-Ph |
| 84 | Me | 2,4-di-Cl-Ph | 4-F-Ph |
| 85 | Me | 2,4-di-Cl-Ph | 2,4-di-F-Ph |
| 86 | Et | 2,4-di-Cl-Ph | 4-Cl-Ph |
| 87 | Et | 2,4-di-Cl-Ph | 2,4-di-Cl-Ph |
| 88 | Et | 2,4-di-Cl-Ph | 4-Br |
| 89 | Et | 2,4-di-Cl-Ph | 3,4-di-Cl-Ph |
| 90 | Et | 2,4-di-Cl-Ph | 4-Me-Ph |
| 91 | Et | 2,4-di-Cl-Ph | 4-CF₃-Ph |
| 92 | Et | 2,4-di-Cl-Ph | 3-Cl |
| 93 | Et | 2,4-di-Cl-Ph | 3-MeO-Ph |
| 94 | Et | 2,4-di-Cl-Ph | 4-F-Ph |
| 95 | Et | 2,4-di-Cl-Ph | 2,4-di-F-Ph |
| 96 | Et | 2,4-di-Cl-Ph | 2-Cl-4-F-Ph |

Methods for preparing the compounds of the present invention are not particularly limited. For example, the compounds can be produced by the following method. In the examples of the specification, the preparations of typical compounds of the present invention will be specifically explained in detail. Therefore, those skilled in the art can readily prepare the compounds of the general formula (I) by referring to the following general descriptions and specific explanations in the examples and appropriately choosing compounds as starting materials, reagents, reaction conditions and so forth, and by optionally adding suitable modifications and alterations to these methods. The reactive functional groups of compounds as starting materials or reagents may be protected with suitable protective groups, if necessary. Such protective groups can be appropriately chosen by those skilled in the art depending on the types of functional groups.

Compound (III) can be produced by reacting Compound (II) with 1,2,4-triazole or an alkali metal salt thereof in a suitable solvent such as acetone, acetonitrile, methanol, ethanol, and dimethylformamide in the presence of a suitable acid trapping agent such as potassium carbonate, sodium carbonate, potassium butoxide, sodium hydride, potassium hydride, sodium methoxide, and sodium ethoxide (in the scheme, Xn represents one or more substituents such as hydrogen atom, chlorine atom, fluorine atom, methoxy group, and Hal represents chlorine atom, bromine atom, or iodine atom).

Compound (IV) can be prepared by reacting Compound (III) with a benzyl halide derivative in a suitable dry solvent such as methanol, ethanol, tetrahydrofuran, and dimethylformamide in the presence of a suitable base such as potassium butoxide, sodium hydride, potassium hydride, sodium methoxide, and sodium ethoxide (in the scheme, Yn represents one or more substituents such as chlorine atom, bromine atom, methyl group, trifluoromethyl group, and methoxy group).

Compound (I) of the present invention can be prepared by reacting an organometallic compound such as alkyl lithium and Grignard reagents with Compound (IV) in an aprotic anhydrous solvent such as tetrahydrofuran, dimethylformamide, diglim, dioxane, and diethyl ether (in the scheme, R¹ has the same meaning as that defined in the formula (I), and preferably represents methyl group or ethyl group, and Xn and Yn have the same meanings as those defined above). In the alkylation of the above reaction, an alkyl lithium or an alkyl magnesium bromide may sometimes give a different ratio of stereoisomers as reaction products. Where methylation is carried out, respective reagents may sometimes give a different diastereoisomer in an approximately 100% yield. Therefore, it is possible to selectively prepare a desired stereoisomer by suitably choosing a reagent.

The compounds of the present invention or salts thereof have specific inhibitory action against the brassinosteroid biosynthesis. Therefore, the compounds of the present invention or salts thereof are useful as, for example, active ingredients of plant growth regulators. The term "plant growth regulation" used in this specification should be construed in its broadest sense, including, for example, dwarfing of plants (suppression of plant elongation), pollen growth inhibition, retention of flower freshness, use of plant anti-stress agents (heat, dryness, coldness or the like), weed control by regulation of reproduction, suppression of plant retrogradation, control of hypertrophy of root and so forth. For example, plant growth dwarfing agents, plant growth retardants, herbicides and so forth are typical examples of the plant growth regulators of the present invention. However, the plant growth regulators of the present invention are not limited to these examples.

The plant growth regulators of the present invention can be formulated, for example, as an agricultural composition by using formulation additives well known in the art. Forms of the agricultural composition are not particularly limited, and any forms that can be used in the art may be chosen. For example, compositions in the forms of emulsions, liquids, oils, water soluble powders, wettable powders, flowables, powders, subtilized granules, granules, aerosols, fumigants, pastes and so forth can be used. The methods for manufacturing the agricultural composition are also not particularly limited, and any methods available to those skilled in the art can be appropriately employed. As the active ingredient of the plant growth regulators of the present invention, two or more of the compounds represented by the aforementioned formula (I) or salts thereof may be used in combination. Further, other active ingredients of agricultural chemicals such as insecticides, fungicides, insecticidal and fungicidal agents, herbicides and the like. Methods of application and doses of the plant growth regulators of the present invention can be suitably chosen by those skilled in the art depending on conditions including a purpose of application, a dosage form, a plot to be treated and so forth.

EXAMPLES

The present invention will be explained more specifically with reference to examples. However, the scope of the present invention is not limited to the following examples.

Example 1

Preparation of the Compound of the Present Invention

To 20 ml of dimethylformamide, 1.99 g of bromoacetophenone, 0.69 g of triazole and 2 g of potassium carbonate were added, and the mixture was allowed to react at room temperature for 16 hours. The reaction mixture was poured into 100 ml of water, and the deposited crystals were separated by filtration. The crystals obtained were recrystallized from hexane/ethylacetate to obtain 2-(1,2,4-triazoyl) acetophenone (yield: 85%).

In 50 ml of dry dimetbylformamide, 1.87 g of 2-(1,2,4-triazoyl)acetophenone was dissolved, and the solution was added with 0.48 g of 60% sodium hydride and stirred for 10 minutes with ice cooling. The reaction mixture was added dropwise with 1.61 g of 4-chlorobenzyl chloride dissolved in dimethylformamide, and then stirred for 2 hours. The reaction was stopped by adding 1 ml of methanol to the reaction mixture, and the solvent was evaporated under reduced pressure. The residue was distributed between water and ether, and the ether layer was separated. The aqueous layer was extracted twice with ether, and the ether layers were combined with the ether layer previously obtained and washed with saturated brine. The ether layer was dried over anhydrous magnesium sulfate, and then the solvent was evaporated under reduced pressure. The residue was purified by silica gel column chromatography (hexane/ethyl acetate) to obtain 2-(4-chlorobenzyl)-2-(1,2,4-triazoyl)acetophenone (yield: 68%).

Under a nitrogen flow, 0.312 g of 2-(4-chlorobenzyl)-2-(1,2,4-triazoyl)-acetophenone was dissolved in 10 ml of dry tetrahydrofuran. This solution was cooled to −80° C. with dry ice/acetone, and added dropwise with 1.1 equivalents of an ether solution of methyl lithium with stirring. The reaction mixture was stirred for 30 minutes, and returned to room temperature. The reaction mixture was poured into an ammonium chloride solution, and extracted three times with ethyl acetate. The organic phase was washed with saturated brine, and dried over anhydrous magnesium sulfate, and the solvent was evaporated under reduced pressure. The residue was purified by silica gel column chromatography (hexane/ethyl acetate) to obtain 4-(4-chlorophenyl)-2-phenyl-3-(1,2,4-triazoyl)butan-2-ol (Compound 1, a mixture of diastereomers, yield: 58%).

The above product was a mixture of two diastereomers (80:20), and each diastereomer was a mixture of equal amounts of enantiomers. Each of the diastereomers can be separated by the aforementioned column chromatography.

$^1$H-NMR ($\delta$, ppm, $CDCl_3$).

Diastereomer (I) (Compound 2)

1.28 (s, 3H), 2.70 (dd, 1H, J=2.6, 14.3 Hz), 3.24 (dd, 1H, J=11.5, 14.3 Hz), 4.38 (s, 1H), OH), 4.42 (dd, 1H, J=2.3, 11.5 Hz), 6.54 (d, 2H, J=8.4 Hz), 7.07 (d, 2H, J=8.4 Hz), 7.32–7.60 (m, 5H), 7.67 (s, 1H), 8.06 (s, 1H).

Diastereomer (II) (Compound 3)

1.62 (s, 3H), 3.33 (dd, 1H, J=3.19, 14.1 Hz), 3.499 (dd, 1H, J=11.5, 14.1 Hz), 4.495 (dd, 1H, J=2.9, 11.5 Hz), 4.71 (s, 1H, OH), 6.78 (d, 2H, J=8.4 Hz), 7.13 (d, 2H, J=8.4 Hz), 7.10–7.26 (m, 5H), 7.236 (s, 1H), 7.799 (s, 1H)

Isomer (I) can be selectively prepared by using methyl magnesium bromide instead of methyl lithium in the aforementioned reaction.

Under a nitrogen flow, 0.312 g of 2-(4-chlorobenzyl)-2-(1,2,4-triazoyl)-acetophenone was dissolved in 10 ml of dry tetrahydrofuran. This solution was cooled to −80° C. with dry ice/acetone, and added dropwise with 1.1 equivalents of an ether solution of methyl magnesium bromide with stirring. The reaction mixture was stirred for 30 minutes, and returned to room temperature. The reaction mixture was poured into an ammonium chloride solution, and extracted three times with ethyl acetate. The organic phase was washed with saturated brine, and dried over anhydrous magnesium sulfate, and the solvent was evaporated under reduced pressure. The residue was purified by silica gel column chromatography (hexane/ethyl acetate) to obtain 4-(4-chlorophenyl)-2-phenyl-3-(1,2,4-triazoyl)butan-2-ol (total yield: 75%).

Each of the aforementioned Isomer (I) and Isomer (II) was a mixture of two enantiomers (1:1). These enantiomers were resolved by using an optical resolution column (Daicel Chemical Industries, Ltd., Chiralcell OJ), and four stereoisomers (2a, 2b/3a, 3b) were finally obtained. Respective NMR spectra of the stereoisomers were the same as those of Isomer (I) and Isomer (II).

NMR spectrum data of the compounds prepared in a similar manner are shown below ($\delta$, ppm, $CDCl_3$, the compound numbers correspond to those mentioned in the above table).

Compound 2, Compound 2a and Compound 2b (Compounds 2a and 2b are enantiomers of Compound 2, the same shall apply hereinafter)

1.28 (s, 3H), 2.70 (dd, 1H, J=2.6, 14.3 Hz), 3.24 (dd, 1H, J=11.5, 14.3 Hz), 4.38 (s, 1H, OH), 4.42 (dd, 1H, J=2.3, 11.5 Hz), 6.54 (d, 2H, J=8.4 Hz), 7.07 (d, 2H, J=8.4 Hz), 7.32–7.60 (m, 5H), 7.67 (s, 1H), 8.06 (s, 1H).

Compound 3, Compound 3a and Compound 3b 1.62 (s, 5H), 3.33 (dd, 1H, J=3.19, 14.1 Hz), 3.499 (dd, 1H, J=11.5, 14.1 Hz), 4.495 (dd, 1H, J=2.9, 11.5 Hz), 4.71 (s, 1H, OH), 6.78 (d, 2H, J=8.4 Hz), 7.13 (d, 2H, J=8.4 Hz), 7.10–7.26 (m, 5H), 7.236 (s, 1H), 7.799(s, 1H).

Compound 4

1.283 (s, 3H), 2.678 (dd, 1H, J=2.7, 14.3 Hz), 3.212 (dd, 1H, J=11.5, 14.3 Hz), 4.368 (s, 1H, OH), 4.417 (dd, 1H, J=2.4, 11.7 Hz), 6.48 (d, 2H, J=8.4 Hz), 7.221 (d, 2H, J=8.4 Hz), 7.48–7.34 (m, 5H), 7.675 (s, 1H), 8.059 (s, 1H).

Compound 5, Compound 5a and Compound 5b 1.771 (s, 3H), 3.317 (dd, 1H, J=3,14.1 Hz), 3.492 (dd, 1H, J=11.5, 14.1 Hz), 4.492 (dd, 1H), J=3, 11.5 Hz), 4.706 (s, 1H, OH), 6.725 (d, 2H, J=8.27 Hz), 7.298–7.138 (m, 8H), 7.805 (s, 1H).

Compound 6

1.294 (s, 3H), 2.917 (dd, 1H, J=2.9, 14.2 Hz), 3.265 (dd, 1H, J=11.6, 14.2 Hz), 4.477 (s, 1H, OH), 4.670 (dd, 1H, J=2.9, 11.5 Hz), 6.416 (d, 1H, J=8.3 Hz), 6.890 (dd, 1H, J=2.0, 8.3 Hz), 7.245 (d, 1H, J=2.0 Hz), 7.633–7.319 (m, 5H), 7.713 (s, 1H), 8.043 (s, 1H).

Compound 7

1.286 (s, 3H), 2.687 (dd, 1H, J=2.8, 14.4 Hz), 3.244 (dd, 1H, J=11.5, 14.4 Hz), 4.285 (s, 1H, OH), 4.433 (dd, 1H, J=2.7, 11.5 Hz), 6.412 (dd, 1H, H=2.0, 8.2 Hz), 6.763 (d, 1H, J=2.0 Hz), 7.151 (d, 1H, J=8.2 Hz), 7.60–7.34 (m, 5H), 7.734 (s, 1H), 8.073 (s, 1H).

Compound 8

1.285 (s, 3H), 2.216 (s, 3H), 2.675 (dd, 1H, J=2.7, 14.3 Hz), 3.171 (dd, 1H, J=11.6, 14.2 Hz), 4.436 (dd, 1H, J=2.5, 11.6 Hz), 4.525 (s, 1H, OH), 6.485 (d, 2H, J=7.8 Hz), 6.90 (d, 2H, J=7.8 Hz), 7.616–7.327 (m, 5H), 7.629 (s, 1H), 8.054 (s, 1H).

Compound 9

1.293 (s, 3H), 2.239 (dd, 1H, J=2.2, 14.3 Hz), 3.338 (dd, 1H, J=11.5, 14.2 Hz), 4.336 (s, 1H, OH), 4.465 (dd, 1H, J=2.5, 11.5 Hz), 6.734 (d, 2H, J=8 Hz), 7.360 (d, 2H, J=8 Hz), 7.613–7.346 (m, 5H), 7.682 (s, 1H), 8.074 (s, 1H).

Compound 10

1.288 (s, 3H), 2.703 (dd, 1H, J=2.4, 14.2 Hz), 3.237 (dd, 1H, J=11.6, 14.2 Hz), 4.399 (s, 1H, OH), 4.456 (dd, 1H, J=2.6, 11.6 Hz), 6.457 (d, 1H, J=7.5 Hz), 6.666 (s, 1H), 6.989–7.102 (m, 2H), 7.611–7.338 (m, 5H), 7.696 (s, 1H), 8.070 (s, 1H).

Compound 11

1.288 (s, 3H), 2.696 (dd, 1H, J=2.4,14.6 Hz), 3.187 (dd, 1H, J=11.5, 14.2 Hz), 3.638 (s, 3H), 4.465 (dd, 1H, J=2.4, 11.5 Hz), 4.509 (s, 1H), 6.113 (s, 1H), 6.213 (d, 1H, J=7.68 Hz), 6.642 (dd, 1H, J=2.4, 8.2 Hz), 7.024 (t, 1H, J=7.9 Hz), 7.615–7.326 (m, 5H), 7.664 (s, 1H), 8.066 (s, 1H).

Compound 12

1.262 (s, 3H), 2.649 (dd, 1H, J=2.6, 14.4 Hz), 3.213 (dd, 1H, J=11.7, 14.2 Hz), 4.358 (dd, 1H, J=2.5, 11.5 Hz), 4.499(s, 1H, OH), 6.534 (d, 2H, J=8.3 Hz), 7.077 (d, 2H, J=8.3 Hz), 7.429 (d, 2H, J=8.4 Hz), 7.537 (d, 2H, J=8.4 Hz), 7.648 (s, 1H), 8.065 (s, 1H).

Compound 13, Compound 13a and Compound 13b 1.738 (s, 3H), 3.321 (dd, 1H, J=3.32, 14.1 Hz), 3.469 (dd, 1H, 11.4, 14.1 Hz), 4.459 (dd, 1H, J=3.1, 11.4 Hz), 4.848 (s, 1H, OH), 6.764 (d, 2H, J=8.4 Hz), 7.130–7.230 (m, 7H), 7.810 (s, 1H).

Compound 14

1.265 (s, 3H), 2.886 (dd, 1H, J=3.0, 14.2 Hz), 3.248 (dd, 1H, J=11.6, 14.2 Hz), 4.582 (s, 1H, OH), 4.6338(dd, 1H, 3.0, 11.4 Hz), 6.409 (d, 1H, J=8.3 Hz), 6.90 (dd, 1H, J=2.1, 8.3 Hz), 7.179 (d, 1H, J=2.7 Hz), 7.414 (d, 2H, J=8.7 Hz), 7.568 (d, 2H, J=8.72 Hz), 7.687 (s, 1H), 8.05 (s, 1H).

Compound 15

1.274 (s, 3H), 2.670 (d, 1H, J=2.7, 14.3 Hz), 3.218 (dd, 1H, J=11.7, 14.3 Hz), 4.359 (dd, 1H, 2.4, 11.5 Hz), 4.457 (s, 1H, OH), 6.537 (d, 2H, J=8.4 Hz), 7.078 (d, 2H, J=8.4 Hz), 7.144 (t, 2H, J=8.5 Hz), 7.569 (dd, 2H), 7.649 (s, 1H), 8.065 (s, 1H).

Compound 16

1.754 (s, 3H), 3.343 (dd, 1H, J=3.2, 11.5 Hz), 3.50 (dd, 1H, J=11.5, 14.2 Hz), 4.478 (dd, 1H, J=3.0, 14.4 Hz), 4.488 (s, 1H, OH), 6.779–7.286 (m, 9H), 7.814 (s, 1H).

Compound 17

1.276 (s, 3H), 2.903 (dd, 1H, J=3.0, 14.2 Hz), 3.245 (dd, 1H, J=11.5, 14.2 Hz), 4.544 (s, 1H, OH), 4.614 (dd, 1H, J=3.0,11.5 Hz), 6.402 (d, 1H, J=8.3 Hz), 6.871 (dd, 2H, J=2, 8.5 Hz), 7.125 (t, 2H, J=8.8 Hz), 7.594 (dd, 2H, J=5.2, 8.9 Hz), 7.688 (s, 1H), 8.049 (s, 1H).

Compound 18

1.272 (s, 3H), 2.219 (s, 3H), 2.653 (dd, 1H, J=2.5, 14.2 Hz), 3.159 (dd, 1H, J=11.5, 14.2 Hz), 4.374 (dd, 1H, J=2.3, 11.5 Hz), 4.596 (s, 1H, OH), 6.476 (d, 2H, J=8.0 Hz), 6.905 (d, 2H, J=7.7 Hz), 7.155 (d, 2H, J=8.0 Hz), 7.576 (dd, 2H, J=5.3, 8.9 Hz), 7.607 (s, 1H), 8.053 (s, 1H).

Compound 19

1.269 (s, 3H), 2.739 (dd, 1H, J=2.6, 14.3 Hz), 3.212 (dd, 1H, J=11.5, 14.2 Hz), 3.854 (s, 3H), 4.335 (s, 1H), 4.361 (dd, 1H, J=2.6, 11.5 Hz), 6.556 (d, 2H, J=8.4 Hz), 6.972 (d, 2H), J=8.9 Hz), 7.069 (d, 2H, J=8.4 Hz), 7.489 (d, 2H, J=8.9 Hz), 7.654 (s, 1H), 8.042 (s, 1H).

Compound 20

1.745 (s, 3H), 3.301 (dd, 1H, J=3.1, 14.1 Hz), 3.486 (dd, 1H, J=11.6, 14.1 Hz), 3.723 (s, 3H), 4.452 (dd, 1H, J=3.1, 11.6 Hz), 4.560 (s, 1H, OH), 6.724 (m, 4H), 7.187 (m, 5H), 7.821 (s, 1H).

Compound 21

1.274 (s, 3H), 2.957 (dd, 1H, J=2.9, 14.2 Hz), 3.251 (dd, 1H, J=11.5, 14.1 Hz), 3.848 (s, 3H), 4.416 (s, 1H), 4.623 (dd, 1H, 2.9, 11.5 Hz), 6.427 (d, 1H, J=8.2 Hz), 6.957 (d, 2H), J=8.4 Hz), 7.047–6.821 (m, 2H), 7.522 (d, 2H, J=8.4 Hz), 7.694 (s, 1H), 8.030 (s, 1H).

Compound 22

0.593 (t, 3H), 1.09 (q, 1H, J=7.14 Hz), 1.68 (q, 1H, J=7.3 Hz), 2.64 (dd, 1H, J=2.74, 14.5 Hz), 3.225 (dd, 1H, J=11.5, 14.4 Hz), 4.201 (s, 1H), 4.44 (dd, 1H, J=2.4, 11.5 Hz), 6.523 (d, 2H, J=8.4 Hz), 7.066 (d, 2H, J=8.4 Hz), 7.56–7.30 (m, 5H), 7.680 (s, 1H), 8.063 (s, 1H).

Compound 23

0.898 (s, 9H), 1.352 (s, 3H), 2.133 (s, 1H, OH), 3.249 (dd, 1H, J=11.5, 13.6 Hz), 3.454 (dd, 1H, J=2.5, 13.6 Hz), 4.374 (dd, 1H, J=2.5, 11.5 Hz), 6.713 (d, 2H, J=8.3 Hz), 7.115 (d, 2H), J=8.3 Hz), 7.612 (s, 1H), 7.950 (s, 1H).

Compound 24

0.833 (s, 9H), 1.456 (s, 3H), 3.228 (dd, 1H, J=3.6, 13.8 Hz), 3.332 (dd, 1H, J=11.3, 13.8 Hz), 3.437 (s, 1H), 4.466

(dd, 1H, J=3.6, 11.3 Hz), 6.747 (d, 2H, J=8.3 Hz), 7.138 (d, 2H, J=8.3 Hz), 7.529 (s, 1H), 7.935 (s, 1H).

Compound 25

0.780 (s, 9H), 1.490 (s, 3H), 3.315 (dd, 1H, J=11.7, 13.7 Hz), 3.529 (dd, 1H, J=3.5, 13.7 Hz), 3.864 (s, 1H), 4.776 (dd, 1H, J=3.4, 11.6 Hz), 6.432 (d, 1H, J=8.2 Hz), 6.89 (dd, 1H, J=2.1, 8.3 Hz), 7.330 (d, 1H, J=2.1 Hz), 7.552 (s, 1H), 7.914 (s, 1H).

Example 2
Inhibitory Action of the Compound of the Present Invention Against Biosynthesis of Brassinosteroid Several Arabidopsis mutants having defects in the brassinosteroid biosynthetic pathway have been isolated, and their common morphological characteristic has been revealed as dwarfism. Arabidopsis mutants such as det2 (de-etiolation) and cpd (constitutive photomorphogenesis and dwarfism) show strong dwarfism manifested as curled leaves in deep green. Although this phenotype disappears when brassinolide is administered externally, other plant hormones such as IAA and gibberellin are ineffective. Based on these findings, the compound of the present invention (Compound 1 obtained in Example 1) was used in Arabidopsis (wild-type, Colombia) germination assay. Screening was performed under a light condition with criteria whether or not the compound generates abnormality 1) which is morphologically similar to mutants in the brassinosteroid biosynthesis and 2) which disappears when brassinolide is administered. It was also examined whether or not the morphological change induced by the test compound was restored to the morphology of wild-type by addition of braassinolide under a dark condition.

The Arabidopsis germination assay was performed as follows. Seeds of wild-type and det were treated at a low temperature (2° C.) for 2 days, and the surfaces were sterilized with 1% NaOCl solution for 2 minutes and washed seven times with sterilized distilled water. The seeds were sown on 1% agar solid medium containing 0.5×Murashige and Skoog (1962) salt and 1.5% (w/v) sucrose in a plastic plate in the presence or absence of the test compound. The wild-type plant and det2 plant were grown in a growth chamber for 16 hours under a light condition (240 mE/m2s) and for 8 hours under a dark condition (25° C.). For the screening experiment, the plate was sealed with Parafilm (American National Can Co., Ltd., Chicago, Ill., USA). For the restoration experiment that required a longer experimental period, the seeds were sown on 1% agar solid medium containing 0.5×Murashige and Skoog (1962) salt and 1.5% (w/v) sucrose in Agripot (Kirin Brewery Co., Ltd.). The plants were grown in a growth chamber for 16 hours under a light condition (240 mE/m2s) and for 8 hours under a dark condition (28° C.).

As a result, induction of deformed seedlings that were morphologically similar to the mutants in the brassinosteroid biosynthesis was observed with the compound of the present invention. Among the test compounds, Compound 1 (also referred to as "RMB-61" in this example) showed the most potent induction of dwarfism at $10^{-6}$ M. However, this effect was negated by simultaneous administration of brassinolide. The results of dose-effect test of RMB-61 revealed that the shapes of the plants came to significantly resemble to those of det2 mutant at a concentration of $10^{-5}$ M or higher. Therefore, in the following experiments, RMB-61 was used and characterized as an inhibitor of the brassinosteroid biosynthesis.

Generally, the biological activity of brassinosteroids is often evaluated by the in vitro rice leaf lamina inclination bioassay (explantation method: Wada et al., Plant Cell Physiol., 22, pp.323–325, 1981; Takatsuto, J. Chromat. A., 658, pp.3–15, 1994) which is highly sensitive and reliable. However, this conventional method is not suitable for analyzing the mechanism of action of brassinosteroid biosynthesis inhibitors. Recently, Fujioka et al. reported a method (whole plant method) in which the rice leaf lamina inclination bioassay is improved as an in vitro system. This method reflects the actual biosynthesis process of brassinosteroids by administration of various precursors of brassinolide. The inhibitory action of the compound of the present invention against the brassinolide biosynthesis was evaluated by the explantation method and the whole plant method.

The rice leaf lamina inclination bioassay was performed essentially according to the procedure reported by Fujioka et al. as mentioned above by using a dwarfed rice plant (Oryza sativa cv. Tan-ginbozu). Seeds were immersed in water for 2 days at 28° C., and germinated seeds were subjected to selection of those having a uniform coleoptile length (about 1 to 2 mm). Five germinated seeds were planted on 30 ml of 1% agar medium contained in a glass jar (inner diameter: 26 mm×60 mm), and incubated under the aforementioned conditions for 3 days. Each test compound for the bioassay was dissolved in ethanol and placed on a lamina in an amount of 0.5 ml by using a microsyringe. After the plants were incubated under the same growth conditions for 2 days, the external angle between the leaf lamina and its sheath was measured by using an annular protractor. Thirty plants in total (6 jars) were used for each treatment.

Figure 1:
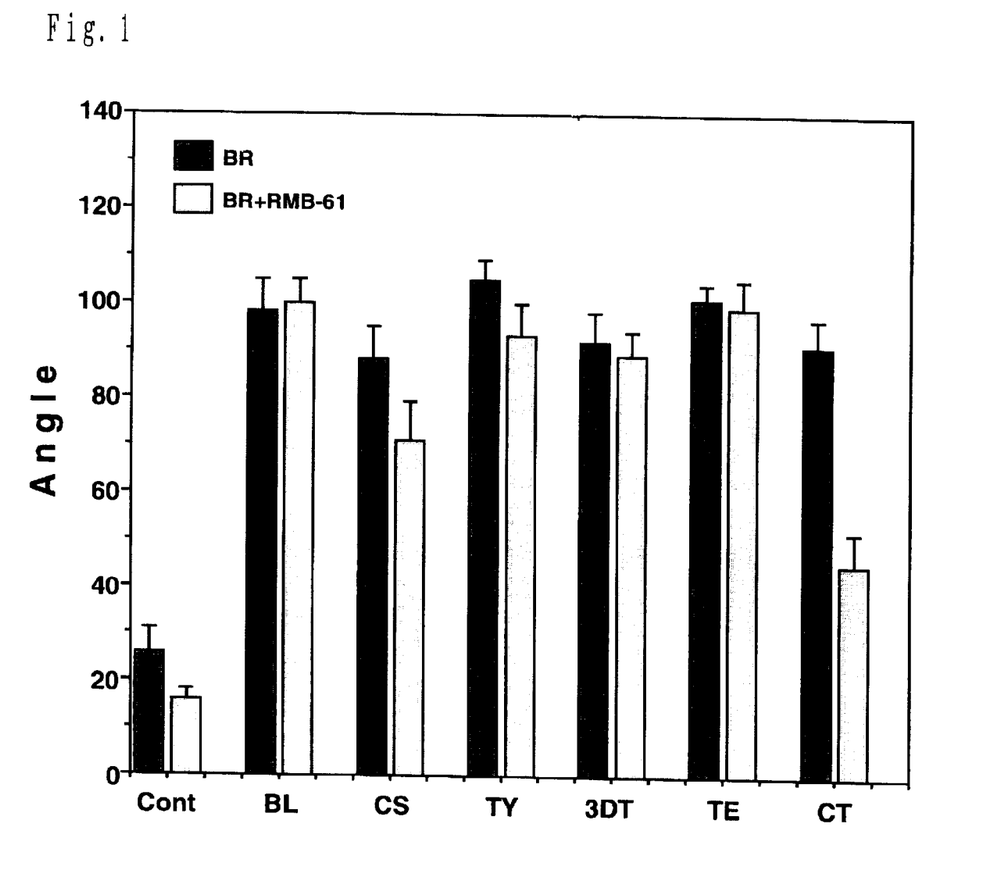
FIG. 1 shows actions of RMB-61 (1 μg/plant) on various brassinosteroids (BR, 0.1 ng/plant) observed in the explantation method. In the figure, "Angle" indicates an inclination angle; and results are indicated with "Cont" for control (no treatment); "BL" for brassinolide (0.1 ng); "CS" for castasterone (1 ng); "TY" for typhasterol (10 ng); "3DT" for 3-dehydroteasterone (10 ng); "TE" for teasterone (100 ng); and "CT" for cathasterone (100 ng) wherein each dose per plant is shown. The dark shaded columns (left) show the results obtained with BR alone, and the light shaded columns (right) show the results obtained with BR+RMB-61.
Figure 2:
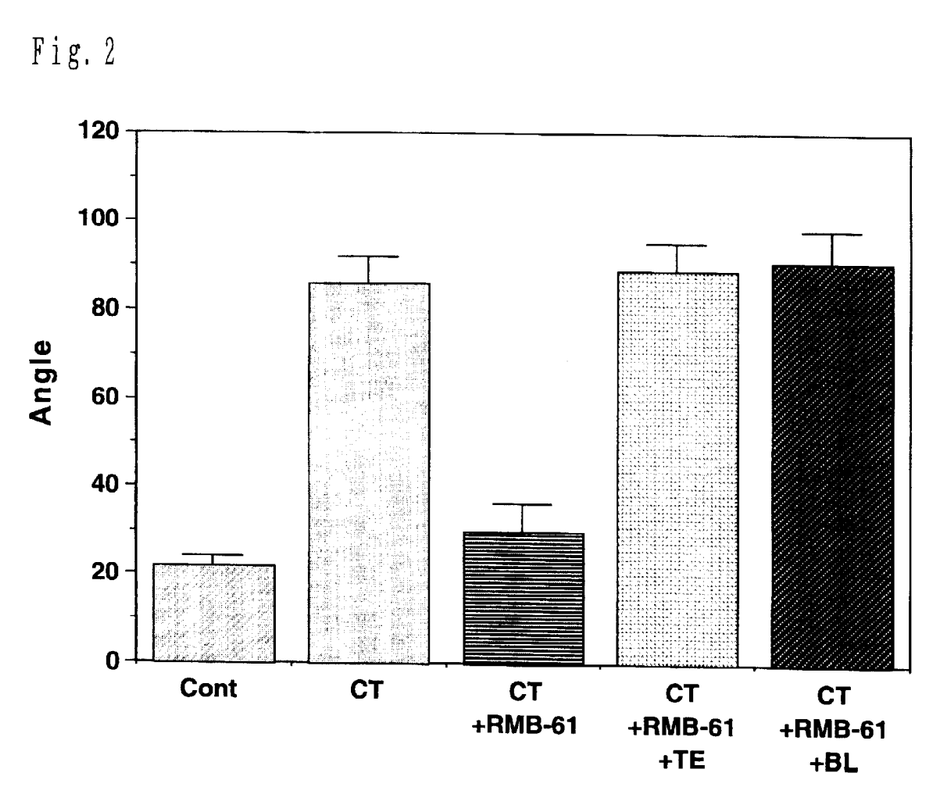
FIG. 2 shows actions of RMB-61 (5 μg/plant) observed in the whole plant method. In the figure, "Angle" indicates an inclination angle; and the results are indicated with "Cont" for control (no treatment); "CT" for cathasterone (100 ng); "TE" for teasterone (100 ng); and "BL" for brassinolide (0.1 ng) wherein each dose per plant is shown.

As a result, absolutely no inhibition of the action of brassinolide by RMB-61 was observed in the explantation method (FIG. 1). Further, in the whole plant method, RMB-61 inhibited the action of cathasterone, which was a precursor of brassinolide, whilst failed to offset the inclination action by teasterone, typhasterol and castasterone (FIG. 2). These results indicate that RMB-61 inhibited the biosynthetic process of brassinosteroid at conversion step from cathasterone to teasterone, and thus stopped the supply of brassinolide in the plants.

In order to confirm the action of RMB-61 also in the Arabidopsis assay, the seeds were grown with addition of the aforementioned brassinolide precursors, and recovery of the growth retardation caused by the RMB-61 treatment was observed. Recent researches on the brassinosteroid biosynthesis in Arabidopsis have revealed that the route starting from campesterol and reaching to castasterone via cathasterone, teasterone and typhasterol constitutes a main pathway accompanied by C-6 oxidation in the early stages of the biosynthesis. Thus, it has been revealed that mutations in these stages can be considered as essential causes of general phenotypes with brassinolide deficiency (Szekeres et al., Cell, 85, pp.171–182, 1996). If RMB-61 is a specific inhibitor against the oxidation of cathasterone, it is expected that the morphological traits of the treated plants have similarities to the phenotypes of the mutants such as cpd (Szekeres et al., Cell, 85, pp.171–182, 1996). It is further expected that the action of RMB-61 will disappear when typhasterol, castasterone or brassinolide is administered, and in addition, the cpd phenotypes caused by brassinosteroids will disappear.

Teasterone, 3-deoxoteasterone, typhasterol, castasterone and brassinolide strongly inhibited the action of RMB-61 in Arabidopsis. However, the growth retardation caused by RMB-61 was maintained in the presence of cathasterone. Similar results were also obtained in the administration experiment under a dark condition. In addition to the growth retardation, RMB-61 promoted greening of plants under weak light. This effect was also eliminated by administration of the aforementioned brassinosteroids except for cathasterone.

Further, rice growth bioassay was performed as follows. Seeds of rice (Oryza sativa cv. Koshihikari) were immersed in tap water for 2 hours, and then 10 seeds were immersed in 2 ml of 10 mM sodium acetate buffer (pH 5.4) containing 10 mM $CaCl_2$ filled in a sterilized 15-ml test tube in the presence or absence of a test compound. The plants were grown in a growth chamber for 16 hours under a light condition (240 mE/m2s) and for 8 hours under a dark condition (25° C.). The plants were collected and the length of shoots was measured.

Uniconazol, which is a gibberellin biosynthesis inhibitor, showed strong growth retardation action for the rice plant based on inhibitory action against the gibberellin biosynthesis, whilst RMB-61 had no effect on the growth of the rice plant. On the other hand, when teasterone or brassinolide was added to the rice plant in which the effect of cathasterone was negated by RMB-61, the response of the rice plant to the brassinosteroid was restored. This results well accorded with the aforementioned results. Further, RMB-61 completely failed to effect the gibberellin treatment, and the results suggest that the target site of RMB-61 is essentially different from that of uniconazol or paclobutrazol, which are strong inhibitors of the gibberellin biosynthesis.

The materials used for the aforementioned methods are as follows.

Plant materials

The de-etiolated 2 (det2) mutant was obtained by uniquely mutating wild-type seeds of the Colombia ecotype and isolating the mutant (Chory et al., Plant Cell, 3, pp.445–459, 1991; Li et al., Science, 272, pp.398–401, 1996). The wild-type seeds (Colombia) were purchased from LHELE Seeds (Round lock, Tex., USA). The seeds of rice (Oryza sativa cv. Koshihikari and Tan-ginbozu) were presented by Dr. I. Honda (National Agriculture Research Center, Tsukuba, Japan).

Test compounds

Brassinolide was purchased from CID-tech Research Inc. (Ontario, Canada). Cathasterone and castasterone were synthesized as described above. Murashige and Skoog salt and vitamin mixture were purchased from GIBCO BRL (Gland Island, N.Y., USA).

As explained above, the morphological change induced by the compound of the present invention disappears when exogenous brassinolide is administered, and the brassinosteroid biosynthesis process, which was inhibited by the compound of the present invention, was found to be a stage preceding the teasterone synthesis. Furthermore, the compound of the present invention did not show growth inhibitory action in the rice elongation test, in which elongation retardation action by paclobutrazol was observed which is a gibberellin biosynthesis inhibitor having a similar chemical structure. Accordingly, it was revealed that the compound of the present invention was a specific inhibitor against the brassinosteroid biosynthesis.

Industrial Applicability

The compounds of the present invention have a specific inhibitory action against the brassinosteroid biosynthesis, and are useful as active ingredients of plant growth regulators and so forth.

What is claimed is:

1. A compound represented by the following formula:

wherein $R^1$ represents a lower alkyl group, $R^2$ represents a phenyl group which is substituted or unsubstituted or a lower alkyl group, and $R^3$ represents a phenyl group which is substituted or unsubstituted, or a salt thereof.

2. The compound or a salt thereof according to claim 1, wherein $R^1$ is methyl group or ethyl group, and $R^2$ represents a phenyl group which is substituted or unsubstituted, or tert-butyl group.

3. 4-(4-Chlorophenyl)-2-phenyl-3-(1,2,4-triazoyl)-butan-2-ol or a salt thereof.

4. An inhibitor against the brassinosteroid biosynthesis which comprises the compound according to claim 1 a salt thereof as an active ingredient.

5. An inhibitor against the brassinosteroid biosynthesis which comprises the compound according to claim 2 or a salt thereof as an active ingredient.

6. An inhibitor against the brassinosteroid biosynthesis which comprises the compound according to claim 3 or a salt thereof as an active ingredient.

* * * * *

UNITED STATES PATENT AND TRADEMARK OFFICE
CERTIFICATE OF CORRECTION

PATENT NO.    : 6,388,089 B1
DATED         : May 14, 2002
INVENTOR(S)   : S. Yoshida et al.

Page 1 of 1

It is certified that error appears in the above-identified patent and that said Letters Patent is hereby corrected as shown below:

<u>Column 14,</u>
Line 39, "An inhibitor against the" should be -- A composition for inhibition of --.
Line 40, after "claim 1" insert -- or --.
Line 42, "An inhibitor against the" should be -- A composition for inhibition of --.
Line 45, "An inhibitor against the" should be -- A composition for inhibition of --.

Signed and Sealed this

Eleventh Day of March, 2003

JAMES E. ROGAN
*Director of the United States Patent and Trademark Office*